United States Patent
Ireland

[19]

[11] Patent Number: 5,855,206
[45] Date of Patent: Jan. 5, 1999

[54] LOOSE PROPHYLACTIC SACK DEVICE HAVING IMPROVED CLOSURE

[76] Inventor: Jud Ireland, 712 N. Foothill Rd., Beverly Hills, Calif. 90210

[21] Appl. No.: 442,586

[22] Filed: May 17, 1995

Related U.S. Application Data

[63] Continuation-in-part of Ser. No. 260,395, Jun. 14, 1994, abandoned, which is a continuation-in-part of Ser. No. 78,514, Jun. 16, 1993, abandoned.

[30] Foreign Application Priority Data

Jun. 10, 1994 [WO] WIPO .................. PCT/US94/06617

[51] Int. Cl.⁶ .................................................. A61F 06/04
[52] U.S. Cl. ....................... 128/844; 128/842; 128/918; 604/349
[58] Field of Search ..................... 128/844, 842, 128/918; 604/330, 347, 348, 349, 350–353

[56] References Cited

U.S. PATENT DOCUMENTS

| | | |
|---|---|---|
| D. 246,119 | 10/1977 | Okamoto . |
| D. 254,808 | 4/1980 | Meldahl ................................. 128/844 |
| 2,358,440 | 9/1944 | Bowman ................................. 604/349 |
| 2,586,674 | 2/1952 | Lonne . |
| 2,604,092 | 7/1952 | Brown et al. . |
| 3,648,700 | 3/1972 | Warner . |
| 3,741,203 | 6/1973 | Liman . |
| 4,254,765 | 3/1981 | Brown et al. . |
| 4,346,699 | 8/1982 | Little et al. . |
| 4,354,494 | 10/1982 | Hogin . |
| 4,363,317 | 12/1982 | Broucek . |
| 4,564,006 | 1/1986 | Pomeranz . |
| 4,601,716 | 7/1986 | Smith . |
| 4,610,245 | 9/1986 | Bieuman . |
| 4,790,834 | 12/1988 | Austin . |
| 4,794,920 | 1/1989 | Robichaud ............................. 128/844 |
| 4,795,425 | 1/1989 | Pugh ...................................... 128/844 |
| 4,798,600 | 1/1989 | Meadows . |
| 4,817,593 | 4/1989 | Taller et al. ........................... 128/844 |
| 4,852,586 | 8/1989 | Haines . |
| 4,869,723 | 9/1989 | Harmon ................................. 128/844 |
| 4,911,151 | 3/1990 | Rankin et al. . |
| 4,961,734 | 10/1990 | Kassman . |
| 4,966,135 | 10/1990 | Renfew . |
| 4,966,166 | 10/1990 | Leffler . |
| 4,981,147 | 1/1991 | Barnett . |
| 4,986,765 | 1/1991 | Caponi . |
| 5,036,863 | 8/1991 | Wheeler . |
| 5,037,779 | 8/1991 | Chapman et al. . |
| 5,074,315 | 12/1991 | McCuiston . |
| 5,137,032 | 8/1992 | Harmon . |
| 5,152,282 | 10/1992 | Elphick et al. . |
| 5,176,152 | 1/1993 | Wheeler . |
| 5,181,527 | 1/1993 | Dorsey et al. . |
| 5,199,444 | 4/1993 | Wheeler . |
| 5,207,233 | 5/1993 | Barner . |
| 5,209,241 | 5/1993 | Hardy . |
| 5,454,379 | 10/1995 | Shephard . |
| 5,458,936 | 10/1995 | Miller et al. ........................... 604/349 |

FOREIGN PATENT DOCUMENTS

| | | |
|---|---|---|
| 938465 | 10/1963 | United Kingdom .............. 604/349 |
| 1250553 | 10/1971 | United Kingdom .............. 128/844 |
| 8902256 | 3/1989 | WIPO . |

OTHER PUBLICATIONS

"How Reliable Are Condoms?", Consumers Reports, May, 1995, pp. 320–325.

"The Market for Condoms", Publisher–Rubber Consultants, 1993, pp. 2:1 and 2:2.

The Great Cover–up—A Condom Compendium, Susan Zimet & Victor Goodman, 1988, Civan, Inc., New York, Lib. Cong. #88–92769.

*What Size is Your Condom?*, Gary M. Griffin, 1990, Added Dimensions Publishers, Los Angeles, CA.

*Primary Examiner*—Robert A. Hafer
*Assistant Examiner*—Justine R. Yu

[57] ABSTRACT

A loose fitting male condom which is held in place by a simple, yet reliable closure. The closure can be a continuous elastic band or a fastening strip. The loose fit makes application and removal easier, and during intercourse increases sensation for the wearer. The closure provides a seal at the base of the penis to protect from disease and pregnancy resulting from fluid leakage, and if suitably tight, can prolong erections.

36 Claims, 5 Drawing Sheets

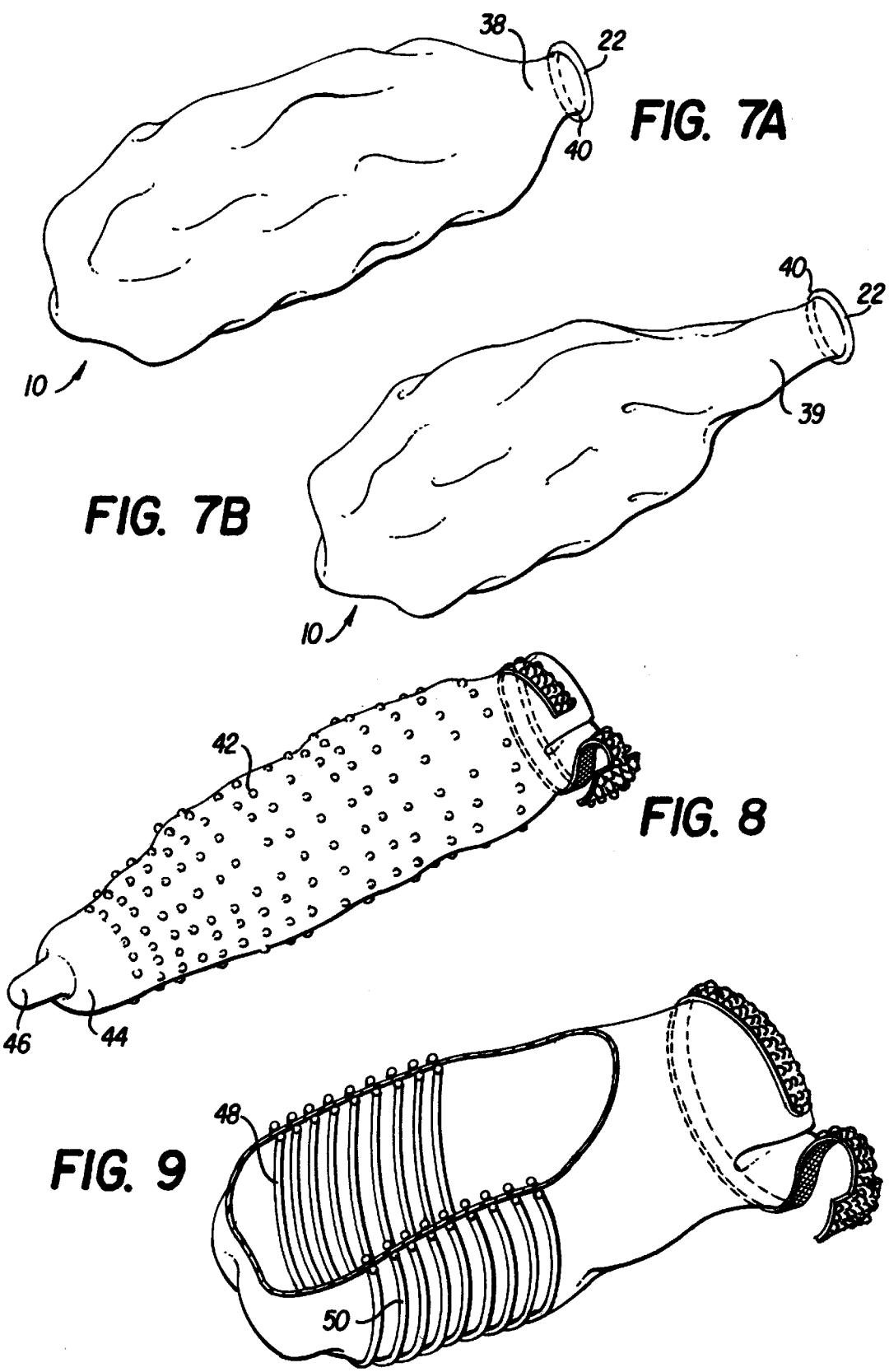

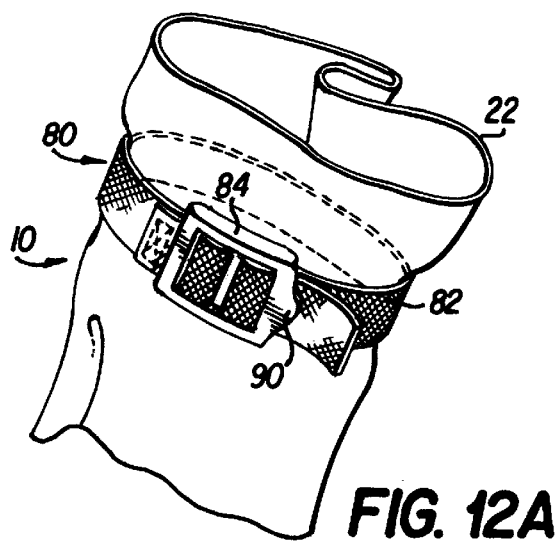 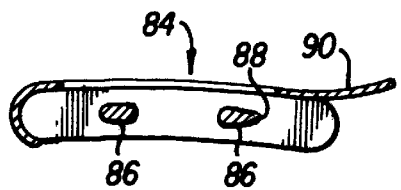
FIG. 12A FIG. 12B
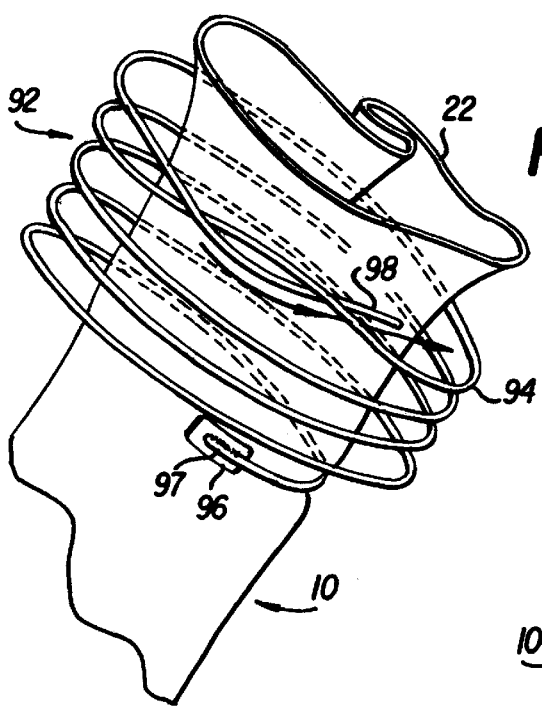 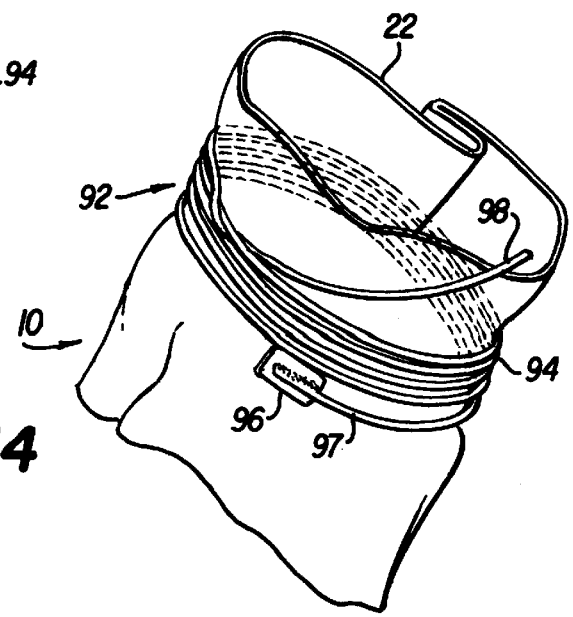
FIG. 13
FIG. 14

LOOSE PROPHYLACTIC SACK DEVICE HAVING IMPROVED CLOSURE

CROSS REFERENCE TO RELATED APPLICATIONS

This is a continuation-in-part of application Ser. No. 08/260,395, filed Jun. 14, 1994, which is itself a continuation-in-part of application Ser. No. 08/078,514, filed Jun. 16, 1993, both now abandoned.

The invention is an improved male condom having easier application and removal, increased sensation for the wearer, improved protection against disease and pregnancy from leakage around the base, and the ability to prolong erection.

BACKGROUND OF THE INVENTION

1. Field of the Invention

Sexually-transmitted diseases today affect millions of people. Because of the threat of AIDS, and other sexually transmitted diseases, condoms are enjoying unprecedented popularity. Although the condom is marketed as one of the few over-the-counter, nonprescription contraceptives, it has its deficiencies. Condoms are uncomfortable. Condoms interfere with lovemaking. Condoms feel unnatural. They interrupt spontaneity. They decrease sexual arousal.

Today, the FDA continues to promote condoms as the most effective protection during intercourse against certain sexually transmitted diseases. In spite of the seriousness of the FDA warnings and the risks involved, a significant fraction of sexually active males, and females decline to use condoms, or use them only occasionally because of their deficiencies, as outlined above.

The present invention relates to a male condom which prevents insemination and the transmission of disease. More specifically, it provides improved ease of application and removal, increased sensation for the wearer, superior protection against disease and pregnancy previously caused by leakage around the base, and the ability to prolong an erection.

2. Description of the Prior Art

The nature of a condom is to form a barrier around the penis, the male organ of sexual intercourse, to prevent direct contact of body parts and fluids which might transmit disease or cause pregnancy. Unfortunately, the contact barrier and snugness of the fit limit tactile sensorial abilities. The decrease in feeling reduces the users' pleasurable sensations, and, therefore, the desire to use a condom.

The average length of an erect male penis is 6 inches. Standard condoms measure 7.5 inches long (excluding reservoir tip). This length is long enough to cover the erect penises of 90% of the male population. In fact, 95% of all men have erect penises less than 8.5 inches long. The circumference of an erect penis also varies within the population. The vast majority of males have penises with circumferences between 87.5 mm (3½ inches) and 150 mm (6 inches).

The majority of condoms sold in the United States closely conform to the same basic shape; the condoms are designed for a snug fit around the penis from the tip, or just below the tip, down to the base. There are two common sizes of condoms sold in the United States. These common sizes are both approximately 190 mm (7.5 inches) long (including reservoir tip) by 104 mm or 108 mm (≈4 inches) in circumference. Another condom, which is more common in Japan, is 165 mm (≈6½ inches) by 87.5 mm (≈3½ inches) in circumference.

A common feature of existing condoms is that they provide a snug fit. Many of these prior art devices have a reservoir tip which helps guard against leakage out of the base by creating a repository for ejaculate.

Conventional condoms, because they are form fitting, are hard to put on and awkward to remove. Most condoms are applied by a rolling on method. The condom is applied to the erect penis before any sexual contact. The condom is placed on the head of the penis and completely unrolled to the base of the penis, ideally using the fingers with dexterity; but many times this is a difficult process and the fingers can cause skin irritation. This process can cause the condom to catch and pull skin and hair during application (and removal), possibly causing condom breakage. Because of their necessary tight fit, condoms often develop a vacuum during the removal process, adding to the difficulty of the removal.

The utility period of a condom usually begins after the penis is erect, and ends just after ejaculation. The utility time period does not extend beyond ejaculation; following ejaculation, the penis is withdrawn while still erect. Manufacturers warn that although it may be romantic to bask in the afterglow while still enjoined, this time is the easiest for the condom to slip off or for seminal fluid to leak out. Thus, prompt removal of the condom after use is uniformly recommended by manufacturers of prior art devices in order to avoid seepage and fluid contact.

In the prior art, sensorial limitations are addressed by using thinner materials of construction. However, although a thinner material improves heat conduction and improves sensation, these thinner materials tend to be less strong, and increase the likelihood of condom failure by breakage.

Variants on the male condom have previously been developed to attempt to address the deficiencies of the prior art devices. In U.S. Pat. No. 4,798,600, Meadows, there is taught a male condom consisting of two segments; one segment is attached firmly to the penis and the other segment slides back and forth over the tip end of the penis as it is repeatedly repositioned during intercourse. Integral to Meadows is a solid ring ("centering means"), positioned at the juncture of these two segments, to anchor the sliding portion. A drawback of Meadow is the use of the solid ring which can be uncomfortable and can move about and inhibit and impede use.

In U.S. Pat. No. 4,564,006, Pomeranz, there is shown a seal or zipper like element running substantially the length of the condom. Pomeranz, as with prior art devices, shows a full length snug fit in order to create the necessary seal. The snug fit is provided by use of a zipper which facilitates the application and removal of the condom. However, the prominent ridge created by the zipper produces an intrusive, unpleasant tactile sensation.

Materials of construction in the prior art are both natural and manmade. Because natural materials, such as animal intestine, are fairly inelastic, the natural material condom, while still designed to be snug fitting, may have added thread elastic around the base such as that found on a male condom sold as Kling-Tite® Naturalamb® Condoms, distributed by Carter Products, New York, N.Y. The Kling-Tite® condom, as with other prior art condoms, is designed to be form fitting, with the thread elastic ineffective for creating a seal; the seal is created by being generally form fitting along the length of the condom.

Still more recently, the use of adhesives has been adopted. For example, a male condom sold as Trojan® Mentor® Safety-Seal™ Condoms, distributed by Carter Products, New York, N.Y, is provided with a ring of adhesive at just above its mid-point. Adhesive is difficult to position and often sticks to unintended locations during application. Because of the difficulty in donning and properly positioning the adhesive ring, an applicator is necessary and is provided with the packaging. Other adhesive condoms typically have the adhesive added at the base, but application of a male condom with any adhesive is difficult and inconvenient.

Accordingly, there has existed a definite need for an improved prophylactic device. The present invention satisfies this need and provides further related advantages.

SUMMARY OF THE INVENTION

In the light of the foregoing, it is an object of the present invention to provide a male condom which offers improved prevention of insemination and the transmission of disease.

A particular object of the invention is to provide condoms which produce a more reliable and secure seal with the base of the penis.

It is a further object to enhance the acceptance and use of the male condom by providing a means for easy and convenient application and removal.

It is yet another object of this invention to increase the level of sensation provided to the users.

Still another object of the invention is to provide for enhancing and prolonging erection and continuing the time of use. Additional objects and advantages will be disclosed by the present invention.

The present invention provides a male condom for protection against pregnancy and sexually transmitted disease, while substantially increasing sensation for the users. The male condom of the present invention is easier and more convenient to apply and remove, and can optionally be employed to enhance and prolong erection and, thereafter, the period of use.

For the present invention there is provided a loose, flexible sheathing in the form of a loose sack which is of greater circumference than the penis. The sheathing flexibility allows the sack to take the form of the erect penis. The loose sack of the male condom of the present invention is between 91 mm (3$^{9}$/$_{16}$ inches) and 255 mm (≈10 inches) long, with a circumference of between 96 mm (3¾ inches) and 186 mm (7$^{5}$/$_{16}$ inches). It is preferably provided in a standard size to fit an erect male penis with the condom having dimensions of 165 mm (6½ inches) in length and 139 mm (5½ inches) in circumference. With these average dimensions it is expected that there will be, on average, 9 mm (⅜ inch) clearance at any given time along the body of the erect penis between the penis and the sheathing, that is the circumference of the loose sack will be 9 mm (⅜ inch) greater than the circumference of the erect penis. More generally, the range for the circumference of the loose sack can be 6 mm to 29 mm greater than the circumference of the erect penis, and the length can be such as to provide at least 12.7 mm (½ inch) clearance in the length at the end of the penis. Thus, it is anticipated that the clearance at any given time (differences in circumferences) between the erect penis and the loose sack will be approximately 2% to 20% of the circumference of the erect penis. That is, the circumference of the loose sack will be 2% to 20% greater than the circumference of the erect penis. For example, if the average erect penis circumference is 130 mm (5⅛ inches) and the clearance between the erect penis and the loose sack at any given time is 9 mm (⅜ inch), 9 mm is approximately 7% of the circumference of 130 mm. Then, the circumference of the loose sack will be 139 mm (5½ inches). Further, the increase in circumference of the loose sack (greater than the circumference of the erect penis) will typically be closer to 2% if lubrication is added. It will also be closer to 2% if the material used is more elastic because the greater the elasticity, the less clearance is desired, while the increase in circumference will be greater, that is, closer to 20%, if a less elastic material is used.

The sack of a male condom of the present invention can also be provided in a larger size of up to 289 mm (≈11$^{5}$/$_{16}$ inches) long and 206 mm (≈8⅛ inches) in circumference to accommodate larger men (5–10% of the population), or for smaller men, as little as 91 mm (≈3½ inches) long and 96 mm (≈3¾ inches) in circumference, considering that the larger size, or smaller size, will provide the same loose fit and clearance dimensions on larger (or smaller) men as the standard size. Extra length may also be added. It is only at the base that the condom is form fitting providing a snug closure for the necessary seal. At the base (open end) of the sack can be a quick closure, which, when the penis is inserted into the sack, provides for ease of closure and binds the base of the sack closely around the penis to form a tight seal at the base.

The closure of a condom according to the invention can be constituted by a strip of a reusable or non-reusable fastening material which can wrap around the base of the sack and then be fastened to itself.

According to other embodiments of the invention, the strip can further include a ring, or buckle, which cooperates with the strip to facilitate creation of a tight seal and constraint around the base of the penis.

According to other embodiments of the invention, the closure is created by forming the base of the condom of an elastically resilient material having a comparatively small circumference. This material will be stretched by the user for placement around the penis and will then be released by the user to contract and, due to its resiliency, tightly grip the base of the penis.

Application of the device of the present invention is made easy, quick and not uncomfortable by the looseness of the sack. The sack eliminates the catching and pulling of the prior art device. It can be put on easily and quickly at any time with a minimum of interruption. Removal of the device is similarly easy, as the closure is simply released and the loose fitting sack freed and readily pulled off.

Unlike the prior art devices which are constricting and are largely immobile relative to the penis, condoms according to the present invention provide a high level of tactile sensation during intercourse, which results from the looseness of the sack. The looseness leaves the penis unconstrained and permits it to slide about within the sack bounds. If desired, lubricant may be added to facilitate movement. The friction from the relative motion of the users, and the device of the present invention, generates increased tactile sensation for both users. The looseness of the fit also is comfortable and promotes a natural feel.

The seals created by condoms according to the invention, which protect against insemination and transmission of disease are provided by the closures, which can cinch down tightly to minimize the likelihood of leaks at the base. Enhanced and prolonged erections of the penis are enabled by the closure, which can be applied tightly enough to restrict the venous blood from flowing out of the penis, both before and after ejaculation, thereby enhancing erection and extending the time of use.

These summary features and other enhancements make the present invention a significant improvement over prior male condoms, and as such will encourage men and women to more frequently utilize this most effective means of protection.

BRIEF DESCRIPTION OF THE DRAWINGS

FIGS. 7A and 7B are side views of two variants of another embodiment of the present invention showing a closure of a continuous elastomeric material integrally attached as a elastomeric neck which narrows near the opening of the sack.

FIG. 8 is a side view of the present invention having further added to the sack textural augmentation in the form of an array of nubs, and a reservoir at its closed end.

FIG. 9 is a side view cut away of the present invention in an unworn and unfurled state having further added to the sack textural augmentation in the form of a series of ridges both the interior and exterior surface.

FIG. 12A is a detail elevational view of an additional embodiment of the present invention.

FIG. 12B is cross-sectional view of a component of the embodiment of FIG. 12A.

FIGS. 13 and 14 are elevational detail views of a further embodiment of the invention with the closure in its unbound and bound states, respectively.

DETAILED DESCRIPTION OF THE PREFERRED EMBODIMENTS

The male condom 10 of the present invention is described in detail in conjunction with the illustrations. It maximizes sensation and prolongs use for the users, while providing for ease of application and removal, and effectiveness for its intended purpose as a contraceptive and disease barrier.

Figure 1:
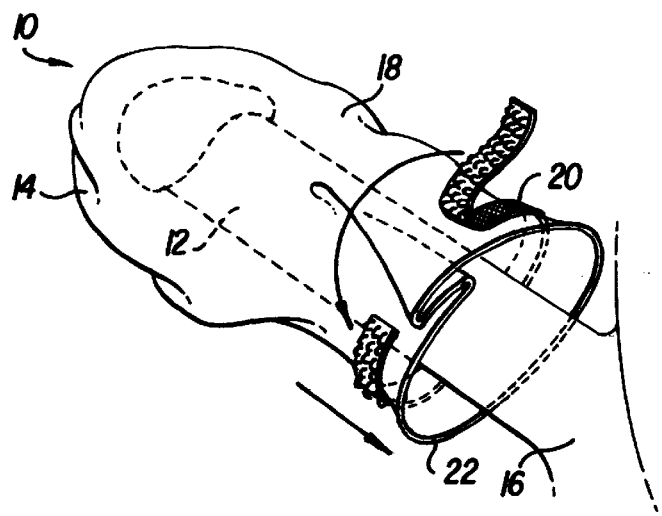
FIG. 1 is an elevational view of one embodiment of the present invention having the closure shown in an unbound state, the condom base in a partly gathered state and the condom at an intermediate point of application.

In FIG. 1 there is shown the male condom 10 of the present invention just before completion of application around erect penis 12. The male condom 10 has two principle components—a sack 14 and a closure 20.

Figure 2:
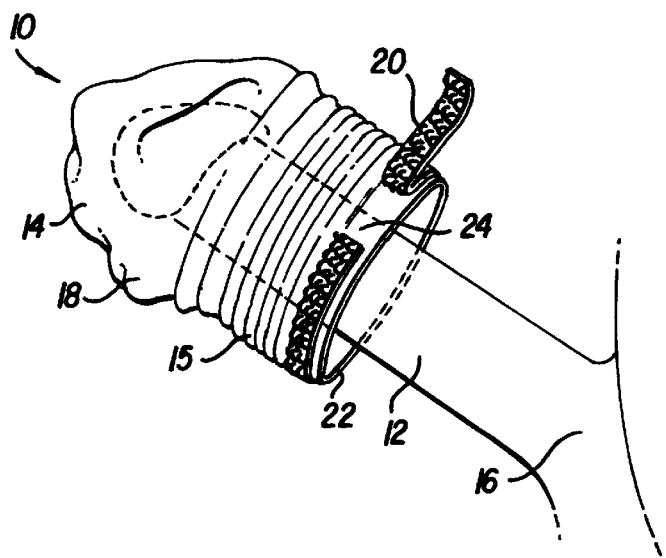
FIG. 2 is an elevational view of an embodiment of the present invention, which differs slightly from that of FIG. 1, at a starting point of application to an erect penis with the closure shown in an unbound state, the condom base ungathered and the sack partially unfurled, as it may appear during application.

The bottom 22 of male condom 10 borders the condom base and is the open end. Closure 20 is located at bottom 22 of male condom 10. Closure 20 is positioned and optionally attached to the sack 14 at the bottom 22 with its length circumscribing bottom 22. As shown in FIG. 2, both bottom 22 and sack 14 fit loosely about erect penis 12 during application. Preferably, loose fit about erect penis 12 is provided by an excess clearance 18 at any one time of about 2% to 20% greater than the circumference of the erect penis. For example, the circumference of sack 14 may be 9 mm (≈⅜ inch) greater than the circumference of erect penis 12.

Figure 4:
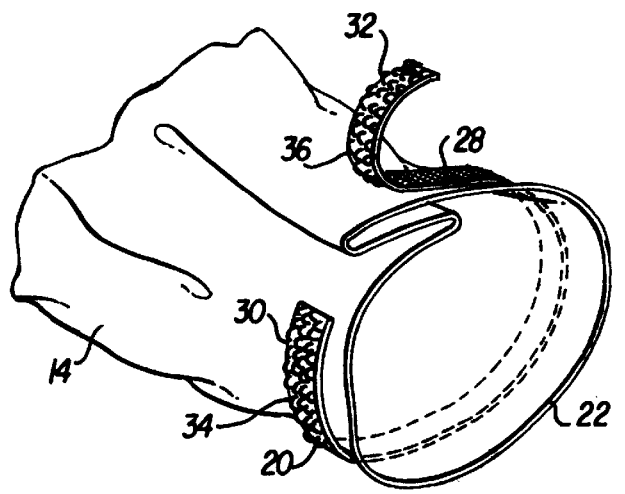
FIG. 4 is an elevational detail view of the closure employed in the embodiments of FIGS. 1–3, the closure being shown in an unbound state.

Referring back to FIG. 2, when bottom 22 is in ungathered and closure 20 is in an unbound state 24, bottom 22 has its full clearance 18 for facilitation of application. After male condom 10 is pulled down over erect penis 12, and excess air removed, bottom 22 is gathered by closure 20 at the base 16 of erect penis 12 thereby reducing the opening at bottom 22 as shown in FIGS. 1 and 4.

Figure 3:
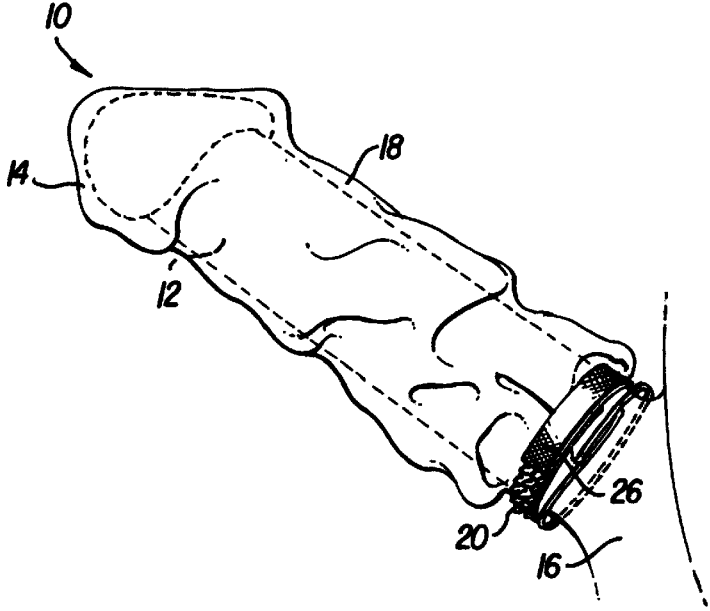
FIG. 3 is another elevational view of the embodiment of FIG. 1, fully applied to an erect penis with the closure means shown in the bound state and the sack fully deployed as it may appear during intercourse.

In FIG. 3 there is shown male condom 10 having bottom 22 now in gathered and bound state 26 and ready for use. Sack 14 still has clearance 18 about erect penis 12, however, the excess air has been released from the inside of sack 14. Seal at the base 16 is effected by closure 20 so that gathered and bound state 26 has no clearance provided around base 16.

For sack 14, the material of construction must be able to withstand push and pull forces of intercourse. A high quality latex, such as, Sheerlon®, which combines strength and maximum protection against breaking or tearing, and thinness for comfort and superior sensation may be used.

All disclosed embodiments of condoms according to the invention can be made of polyurethane, thermoplastic elastomer (TPE), natural rubber latex, or other suitable natural or synthetic materials.

Figure 6:
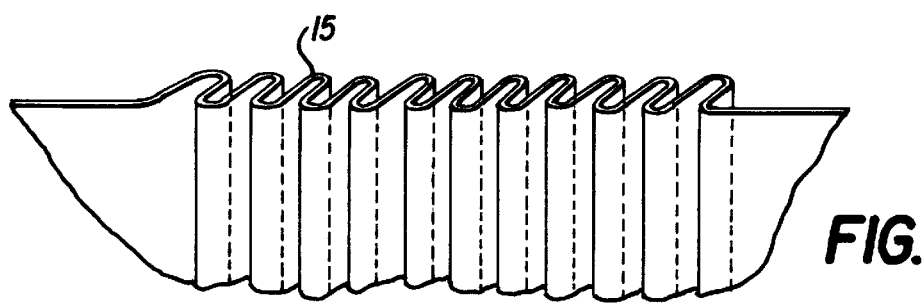
FIG. 6 is a detail of a cross-section through the unfurled sack, illustrating a pleated formation useful in packaging and for ease of application.

As shown in FIGS. 2 and 6, to further facilitate application sack 14 may be provided with a pleated formation 15. A detailed view of pleat formation 15 which may be added to the surface of the sack 14 is shown in FIG. 6. The function of pleat formation 15 is to aid in the gathering of quantities of the sheathing of the sack 14 into a convenient and more manageable form.

Referring again to FIG. 4, closure 20 preferably consists of a material strip 28, possibly elastically resilient, or stretchable, in nature, having two ends—interior strip end 30 and exterior strip end 32. Closure 20 may be a hook and loop type fastening material, such as elastic or inelastic Velcro™, formed into a strip approximately ¼ inch to 1 inch wide. Material strip 28 is preferably thin to minimize its noticeability to the users. Velcro™ does not catch or pull pubic hair for either party, and therefore does not interfere with enjoyable sensations. Interior strip end 30 is covered on its outside with hook material 34. Exterior strip end 32 is covered on its inside surface with loop material 36. The respective relationship between the interior and exterior strip ends 30 and 32 and the hook and loop materials 34 and 36 can be reversed. However, as loop material 36 is more flexible and is therefore easier to grip with the finger tips, loop material 36 is better suited to the exterior strip end 32, as it will be the piece of the closure 20 manipulated during application and removal. The terminus of the external strip end 32 may be slightly wider than the rest of the closure 22, being about ¾ inch wide to be easily grasped by the thumb and forefinger.

Figure 5:
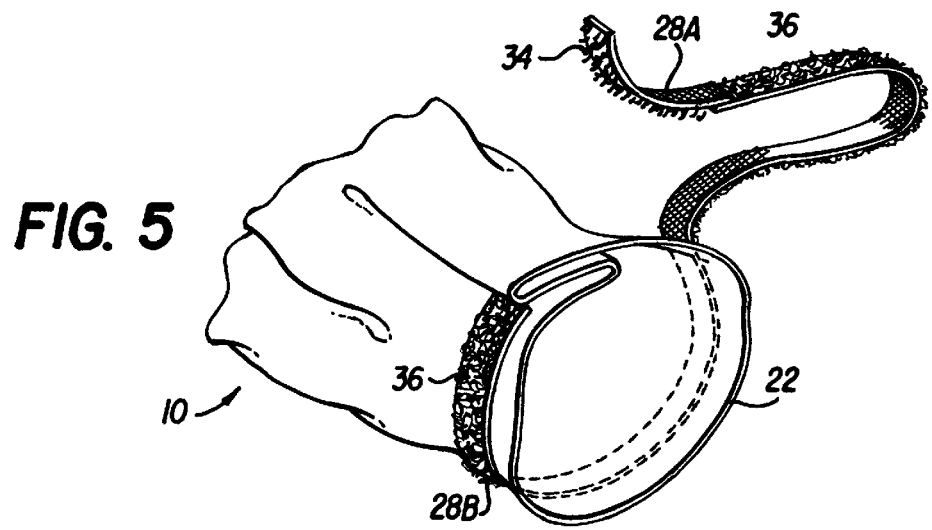
FIG. 5 is a view similar to FIG. 4 showing another embodiment of a closure according to the present invention.

Another embodiment of a condom according to the invention is shown in FIG. 5, which is a detail view showing the base of a condom 10 that is identical to the condom 10 of FIG. 1. In this embodiment, the closure is composed of two separate strips 28A and 28B which are joined end-to-end in any suitable manner, as by sewing, thermal bonding, adhesive bonding, etc, to form a composite strip. Strip 28A carries, on at least part of its interior surface, a length of hook material 34, while strip 28B carries, on at least part of its exterior surface, a length of loop material 36. Preferably, hook material 34 extends along the entire length of strip 28A and loop material 36 extends along the entire length of strip 28B. Strip 28B is fastened, preferably along a portion of its length, to the outer surface of condom 10 in any suitable manner, as by thermal or adhesive bonding. The portion of the length of strip 28b which is fastened to the outer surface of condom 10 preferably extends from the free end of strip 28B to an intermediate point around the circumference of the condom base. The composite strip 28A, 28B have a length greater than the ungathered circumference of the condom base and in any case preferably has a length of at least 65 mm (2½ inches).

The hook material and loop material can be interchanged between strips 28A and 28B. This is also true for all other embodiments disclosed herein which employ hook and loop fasteners.

For closure 20, and other similar closures to be described below, other materials can be used in place of hook material 34 and loop fastening material 36. In particular, adhesive strips can be employed (not shown). Such adhesive strips can be of foam rubber, or foam plastic, or other plastic, covered with adhesive material. If reusable adhesive material is used, the exterior strip end can be simply pulled off of the interior strip end, the male condom 10 donned, and the exterior strip returned to its bound position.

If the adhesive material is not reusable, a protective guard strip must cover the adhesive end(s) until the erect penis 12 is in the male condom 10 and ready to be in its gathered and bound state 26.

Other nonadhesive, reusable fastening materials can be used for the closures of condoms according to the invention. To cite one nonlimiting example, the fastening material for the closure can be of a type provided with "mushroom" type fastening elements as disclosed in U.S. Pat. No. 5,212,853.

The application procedure for the male condom 10 is easy and fast, causing little interruption. To don the male condom 10, the wearer slips the bottom 22 over the erect penis 12, and holding the wide, external strip end 32 of closure 20, pulls it tightly around the base of the erect penis 12 to overlap internal strip end 30. This comfortably, but securely seals closure 20 and bottom 22 about the base of the penis 12 in gathered and bound state 26.

When thus sealed, if sufficient tension was applied when the strip ends 30 and 32 were overlapped, the venous flow of blood from the erect penis 12 will be restricted which can cause maintenance of erection, possibly beyond ejaculation.

To doff male condom 10, the wearer pulls on the exterior strip end 32 which releases the gathered and bound state 26 breaking the seal at bottom 22 about base 16. At this point, male condom 10 condom can be easily slid off.

While in use, the closure 20 is in its gathered and bound state 26 creating a tightly sealed bottom 22 around erect penis 12, as shown in FIG. 3. It is this seal which prevents transmission and commingling of fluids between the users.

When male condom 10 is in use, sack 14 will generally be completely unfurled and the pleat formation 15 shown in FIGS. 2 and 6 will not remain. In some cases, condom 10 will have a circumference 20% greater than that of the erect penis. Increased length, in addition to excess interior space 18, may optionally be added. The increased length may be approximately 51 mm to 64 mm (2 to 2½ inches). This combines with the excess clearance 18 to provide a looseness which further allows erect penis 12 to move freely within the sack 14 during the motions of intercourse. This movement of erect penis 12 relative to the sack 14 produces pleasurable sensations superior to those provided by conventional condoms.

FIG. 7A illustrates another preferred embodiment of a closure according to the invention. At bottom 22 condom 10 is provided with a narrowed, tubular portion 38 preferably extending approximately 25 mm (1 inch) from the end of male condom 10. At bottom 22, there is a sealing and gripping element 40 which together with the narrowed portion 38 seals male condom 10 to an erect penis. Preferably element 40 is of the nature of a continuous elastic band, attached to the loose sack, the elastic band having tension sufficient to grip the base of erect penis 12 firmly enough to form the necessary seal.

FIG. 7B shows a variant of the embodiment of FIG. 7A having a narrowed portion 39 which is longer than narrowed portion 38 of FIG. 7A. In all other respects, the variant of FIG. 7B is identical to that of FIG. 7B.

The height, or length, perpendicular to the circumference, of narrowed portion 38 or 39 in the embodiments of the type shown in FIGS. 7A and 7B may be between 0.8 mm (1/32 inch) and 76 mm (3inches). If the length of portion 38 or 39 is at least 19 mm (¾ inch), sealing and prevention of slippage relative to the penis will be achieved with a high degree of reliability. To cite two nonlimiting examples, narrowed portion 38 of FIG. 7A may have a length of 25.4 mm (1 inch) and narrowed portion 39 of FIG. 7B may have a length of 76 mm (3 inches), of which a portion may be rolled up thus giving element 40 the form of an O-ring.

With respect to embodiments of the type shown in FIGS. 7A and 7B, narrowed portion 38 or 39, including continuous elastic band 40, may have an approximate circumference between 65 mm (≈2½ inches) to 120 mm (≈4¾ inches). Preferably, the circumference of narrowed portion 38 or 39 is <114 mm (4½ inches), and more preferably is <110 mm (4⁵⁄₁₆ inches) and >90 mm (3⁹⁄₁₆ inches). According to exemplary embodiments of the invention, continuous elastic band 40 is preferably 100 mm (4 inches) in circumference (smaller for men with smaller erect penises, and larger for men with larger erect penises).

The circumference of the main portion of condom 10, aside from narrowed portion 38 or 39, is preferably >110%, and not more than 175%, of the circumference of narrowed portion 38 or 39. The main portion of condom 10 preferably has a circumference >110 mm (4⁵⁄₁₆ inches) and more preferably >114 mm (4½ inches). In all cases the circumference of narrowed portion 38, 39 and the continuous elastic band is less than the circumference of the remainder of condom 10.

In the embodiments of FIGS. 7A and 7B, element 40 may be constituted by a separately manufactured O-ring which is thermally or adhesively bonded to bottom 22. In the latter case, O-ring 40 can have an unstretched circumference less than 100 mm (≈4 inches) and can be of a material selected to have any desired resistance to stretching, or restoring force, and/or to be stretchable to any desired extent.

Embodiments of the type shown in FIGS. 7A and 7B can also be made by thermally or adhesively bonding together two pieces of different materials: a first material forming ring 40 and narrowed portion 38 or 39; and a second material forming the main, or large circumference, portion of condom 10. This permits optimum selection of materials for each condom part. In particular, the first material can be selected to provide optimum sealing and gripping and the second material can be selected to provide optimum transmission of physical sensations, each material also being selected to provide appropriate resistance to breakage, tearing and tissue irritation.

Male condom 10 may be further enhanced by having a variety of widths and lengths to accommodate individual variations in penis size and personal preference. Also may be added different types of lubricants.

A number of additional enhancements may be used with present invention. In FIG. 8 there is shown nubs 42 which add an additional stimulating texture to the wearer and his partner. Independent of nubs 42, FIG. 8 also shows a narrow tip 44 which can be added. However, the narrow tip 44 grips approximately the top 2 inches of erect penis 12, reducing the relative motion of erect penis 12 and sack 14, and therefore the stimulation. However, the looseness of the sack 14 continues to provide enhanced stimulation for the remaining lower portion of the erect penis 12. Embodiments provided with a narrow tip 44 may also be provided with a reservoir 46 for capturing ejaculate.

FIG. 9 shows another variation of stimulating texture. Interior ridges 48, which would provide stimulation primarily for the wearer, and exterior ridges 50 which would provide stimulation primarily for the wearer's partner can be included together or singly.

Figure 10A:
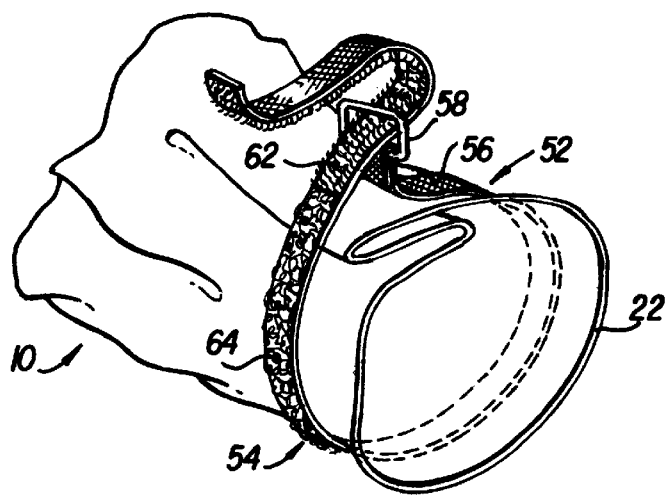
FIGS. 10A and 10B are, respectively, an elevational detail view and an elevational view of a further embodiment of the present invention.
Figure 10B:
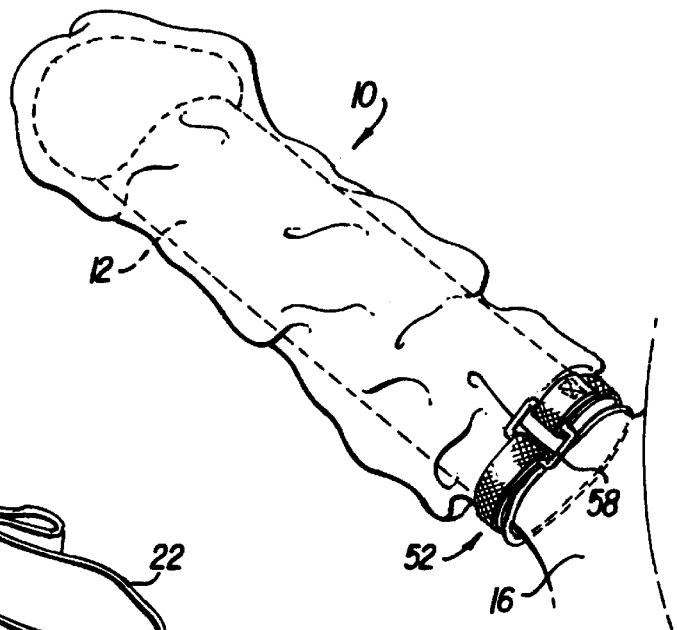

Another embodiment of a closure according to the invention is illustrated in FIGS. 10A and 10B. In FIG. 10A, only the condom bottom 22, the condom base and a portion of the remainder of condom 10 are shown, along with a closure 52 according to this embodiment.

Closure 52 includes a strip 54 of flexible material, which may possibly be elastically resilient, or stretchable, and which may generally have the same physical properties as strip 28 of the embodiments shown in FIGS. 1–4. Strip 54 is fastened to the outer surface of the condom base, preferably only in a limited region 56 adjacent a first end of strip 54. As will become more readily apparent from the further description to be presented below, if the fastening of strip 54 to the condom base is limited in this manner, the extent to which the condom base can be closed around the circumference of a penis will be increased.

Closure 52 further includes a ring member 58 which is preferably of a rigid or semi-rigid material and which, in the illustrated embodiment, has a generally rectangular form. Ring member 58 is constituted by two pairs of opposed sides which enclose an opening.

A first end of strip 54 extends around one side of ring 58 and is then fastened to an adjacent portion of strip 54 to form a closed loop via which strip 54 is fastened to the one side of ring member 58. Fastening of the first end of strip 54 to an adjacent portion of strip 54 can be effected in any suitable manner, such as by sewing, heat sealing, adhesive bonding, thermowelding, etc. Any other suitable fastening technique may be employed. From region 56, strip 54 extends around the circumference of the condom base and a second end 60 of strip 54 can be inserted through the opening provided in ring member 58 and can then be directed around a side of ring member 58 which is opposite to the side which is enclosed by the closed loop formed adjacent the first end of strip 54.

Strip 54 has a first intermediate portion adjacent second end 60 and a second intermediate portion between the first intermediate portion and the first end of strip 54. The first intermediate portion carries, on the surface of strip 54 which will normally face away from condom 10, i.e. the exterior surface of strip 54, a length of hook material 62, while the second intermediate portion carries, at the same surface of strip 54, a length of loop material 64, hook material 62 and the loop material 64 forming components of a hook and loop type fastening material of the type described earlier herein with respect to FIG. 4. Loop material 64 may extend to a point adjacent the closed loop formed at the first end of strip 54 so as to maximize the ability of the closure to form a seal even with a penis having an abnormally small diameter.

The manner in which enclosure 52 would be employed is believed to be self-evident. Second end 60 of strip 54 is inserted through the opening provided by ring member 58 and is then drawn around the associated side of ring member 58, pulling at least part of the first intermediate portion of strip 54, and possibly a part of the second intermediate portion of strip 54, through the opening of ring member 58. Thus, strip 54 is tightened around penis base 16, as shown in FIG. 10B. After strip 54 has been pulled through the opening in ring member 58 to the desired extent, hook material 62 is brought into contact with loop material 64 in order to secure closure 52 in the bound state.

The embodiment shown in FIGS. 10A and 10B enables a particularly tight seal to be formed with relative ease. When tension is applied to second end 60 of strip 54, the result will be an automatic tightening of closure 52 around base 16 because ring member 58 will automatically transmit the tensile force to the first end of strip 54.

The second end of strip 54 can be pulled in a manner to tighten closure 52 around the condom base to any desired degree: firstly, to form a secure seal with the penis; and, secondly, to achieve any desired degree of restriction of venous blood flow from the erect penis.

Figure 11:
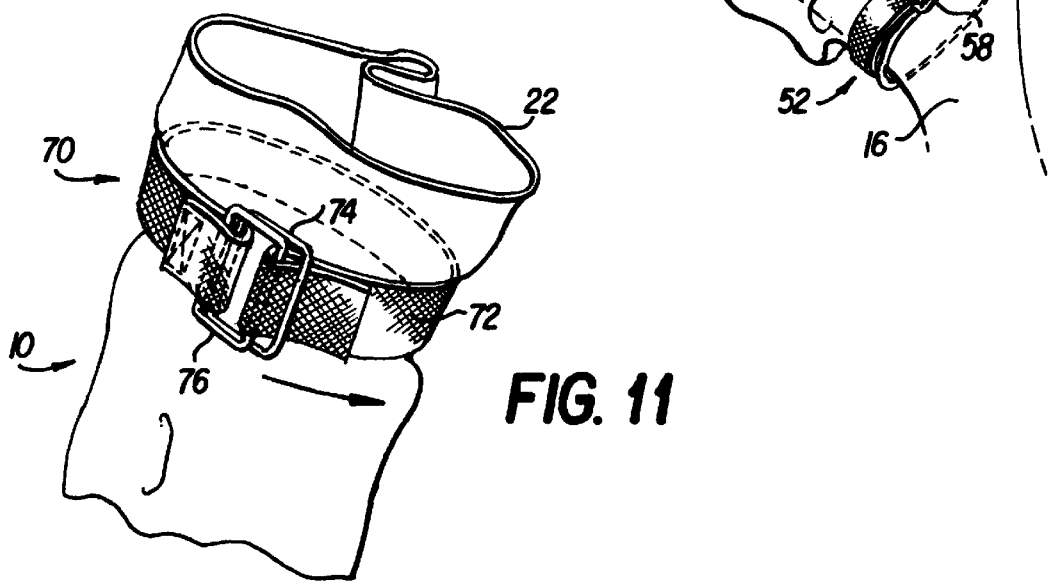
FIG. 11 is a detail elevational view of another embodiment of the present invention.

FIG. 11 shows another embodiment of a closure 70 according to the invention at the base of condom 10. Closure 70 includes a strip 72 of flexible material and a buckle composed of an inner ring 74 and an outer ring 76. In this embodiment, strip 72 is not provided with any type of fastening material and is mechanically gripped by the buckle to hold closure 70 in the bound state.

Strip 72 preferably has a small thickness and is preferably of a substantially inextensible material having a high tensile strength. Strip 72 may alternatively be of a material having some degree of elastic resiliency.

Each of rings 74 and 76 may be made of any suitable plastic or metal and is preferably rigid or semi-rigid. Each ring has a circular cross section and may be in the form of a D ring.

Closure 70 is assembled by wrapping one end of strip 72 around a first leg of each of rings 74 and 76 and then securing strip 72 to itself, as by sewing, thermal bonding, adhesive bonding, etc., in order to form a closed loop. The other end of strip 72 extends between the outer surface of condom 10 and a second leg of each of rings 74 and 76, the latter legs being opposite to and spaced from, the first-mentioned ring legs. The free end of strip 72 is then passed over the second leg of outer ring 76 and under the second leg of inner ring 74. The free end of strip 72 provides a finger grip for the user to enable closure 70 to be tightened and retained in the bound state.

The free end of strip 72 can be pulled in a manner to tighten closure 70 around the condom base to any desired degree: firstly, to form a secure seal with the penis; and, secondly, to achieve any desired degree of restriction of venous blood flow from the erect penis.

To release closure 70 after use, the user may insert the nails of the thumb and index finger of either hand between rings 74 and 76 at opposite sides of the buckle and then urge ring 76 outwardly away from ring 74. This will release the gripping force on strip 72 and allow the closure to be opened.

Another embodiment of the invention is shown in FIGS. 12A and 12B and includes a closure 80 of a type similar to closure 70 of FIG. 11. Closure 80 includes a strip 82 which may be identical to strip 72 of FIG. 11 and a buckle 84 which differs structurally from the buckle of the embodiment of FIG. 11.

Buckle 84 is a rigid or semi-rigid member having a main part in the form of a generally rectangular frame and having two retaining bars 86, shown in FIG. 12B, which extend parallel to one another between a first pair of opposed sides of the main part. The form of buckle 84 in cross section is of a type commonly known as a ladder lock.

One end of strip 82 is placed around one of the retaining bars 86 and under one side of a second pair of sides of the main member. At this end, strip 82 is secured to itself, as by sewing, thermal bonding, adhesive bonding, etc., to form a closed loop which is permanently secured to the associated retaining bar 86.

At the other side of buckle 84, the second end of strip 82 is passed under a second side of the second pair of opposed sides of the main part, around a second one of retaining bars 86, and then back under the second side of the second pair of opposed sides of the main part. The second end of strip 82 is not secured to itself and is movable relative to buckle 84.

With closure 80 in the condition shown in FIG. 12A, condom 10 can be placed over the penis until end 22 is brought to the base thereof and the second end of strip 82 can then be gripped between the thumb and finger of a user and pulled to securely seal the condom base 22 about the base of the penis in a gathered and bound state. This embodiment, like the embodiment of FIG. 11, offers the possibility of producing any desired gripping force to restrict venous blood flow.

As shown in FIG. 12B, the second one of retaining bars 86 may be provided with a row of teeth 88 for gripping strip 82 in order more securely hold closure 80 in the bound state. In addition, the main part of buckle 84 is provided with a protruding portion 90 which curves slightly away from strip 82. By inserting a fingernail under protruding portion 90, the user can easily lift the associated side of buckle 84 to release closure 80 from its bound state.

It will be noted that in the embodiments of FIGS. 11 and 12, the closure 70, 80 need not be attached to condom 10. However, to prevent closure 70, 80 from being lost, a portion of strip 72, 82 could be permanently secured to the outer wall of condom 10 by any one of the fastening techniques mentioned above. A third embodiment of the invention is shown in FIGS. 13 and 14. This embodiment includes a closure 92 which is characterized by extreme structural simplicity. Closure 92 consists essentially of a relatively long cord 94 and an attachment element 96. Attachment element 96 is made of any suitable material that can be permanently bonded to condom 10, as by thermal bonding, e.g. heat sealing, adhesive bonding, etc. Cord 94 can be made of any suitable flexible material which is either inelastic or elastically resilient. Cord 94 has an attachment end 97 which is permanently secured to element 96 by any suitable means, as described earlier herein, as well as a free end 98. Cord 94 is of a length sufficient to encircle the circumference of condom 10 a plurality of times.

FIG. 13 shows closure 92 in a condition in which the condom base is only partially gathered and closure 92 is unbound. In this state, condom 10 can be placed in position around a penis. It will be noted that at this time, free end 98 of cord 94 has been tucked under one turn of the coiled cord so as to extend along a path which passes between that turn and the outer surface of condom 10.

With condom 10 in place, the user need then only exert an appropriate tension force on free end 98 to further gather the condom base and place closure 92 in a bound state. Here again, the tensile force exerted on free end 98 of cord 94 will determine the level of force with which condom 10 is pressed against the base of the penis. Closure 92 will be retained in the bound state by a clamping force created on a portion of cord 94 adjacent free end 98, which force exists between the outer surface of condom 10 and the turn of cord 94 around which free end 98 was previously wrapped.

In order to facilitate release of closure 92 from the bound state, the portion of cord 94 adjacent free end 98 could be secured to an adjacent turn of cord 94 by a slipknot of the type which can readily be untied by pulling on free end 98.

As in the case of the embodiments shown in FIGS. 11 and 12, the embodiment of FIGS. 13 and 14 permits any desired sealing force and degree of restriction of venus blood flow.

One feature of the closures shown in each of FIGS. 10, 11, 12 and 13–14, is that they can constrict the condom base to any desired arbitrarily small diameter, thereby facilitating the establishment of an effective seal, and being capable of effectively restricting venous blood flow, even in the case of penises having an unusually small diameter, as well as those having a large or average diameter. Since strips 72 and 82 of FIGS. and 12 and cord 94 of FIGS. 13 and 14 are held in place purely by mechanical forces, they need not be provided with any type of fastening material or adhesive material.

In all embodiments of the invention, the condom can have some tapering in the vicinity of the tip.

In those embodiments where the closure is in the form of an attachment strip, the strip may or may not be attached to the condom and may or may not be elastically resilient, or stretchable.

The present invention has been described above in terms of a presently preferred embodiment so that an understanding of the invention can be conveyed. There are, however, many configurations for apparatus of male condom 10 not specifically described herein, but with which the present invention is applicable. The present invention should therefore not be seen as limited to the particular embodiment described herein. Accordingly, modifications and variations to which the invention is susceptible may be practiced by those skilled in the art in view of the description herein, without departing from the scope and intent of the following claims.

I claim:

1. A condom having an outer and inner surface and having a generally tubular shaped portion attached to a loose fitting sack portion closed at one end comprising:

a closure portion being resiliently stretchable and dimensioned for secure attachment when used to assure sealing and prevention of slippage, a loose-fitting sack portion having a closed end and an open end and having a length between said closed end and said open end and a circumference, said closure portion being cylindrical and having a first end joined to the open end of the loose-fitting sack portion and a second end remote from said first end, said closure portion having a substantially uniform circumference which is less than the circumference of said sack portion, said loose-fitting sack portion having a lubricant on the outer surface and being easy to apply and unrestrained when used, and said closure portion having a length between said first end and said second end which is less than the length of said sack portion, whereby the shaft of the user below the glands is exposed to movement and stimulation within the loose fitting sack portion of the condom.

2. The condom of claim 1 wherein the circumference of said sack portion is between 110% and not more than 175% of the circumference of said closure portion.

3. The condom of claim 2 wherein said condom is made of material selected from the group consisting of natural rubber latex and thermoplastic elastomers.

4. The condom of claim 3 wherein said material is polyurethane.

5. The condom of claim 1 wherein the circumference of said sack portion is greater than 125% and less than 150% of the circumference of said closure portion.

6. The condom of claim 5 wherein said condom is made of a material selected from the group consisting of natural rubber latex and thermoplastic elastomers.

7. The condom of claim 6 wherein said material is polyurethane.

8. The condom of claim 1 having a length between said closed end of the sack portion and said second end of said closure portion of from 6½ inches to 11 5/16 inches.

9. The condom of claim 8 wherein said closure portion has a length not greater than 3 inches.

10. The condom of claim 9 wherein said closure portion has length of not less than 1 inch.

11. The condom of claim 9 wherein said closure portion has a length of not less than ¾ inch.

12. The condom of claim 9 wherein said closure portion has a length of not less than 1/32 inch.

13. The condom of claim 9 wherein the circumference of said sack portion is equal to or greater than 110% and not more than 175% of the circumference of said closure portion.

14. The condom of claim 13 wherein said condom is made of a material selected from the group consisting of natural rubber latex and thermoplastic elastomers.

15. The condom of claim 14 where the material is polyurethane.

16. The condom of claim 9 wherein the circumference of said sack portion is greater than 125% and less than 150% of the circumference of the said closure portion.

17. The condom of claim 16 wherein said condom is made of a material selected from the group consisting of natural rubber latex and thermoplastic elastomers.

18. The condom of claim 17 wherein said material is polyurethane.

19. The condom of claim 8 wherein said closure portion has a length not greater than 2 inches.

20. The condom of claim 19 wherein said closure portion has a length not less than 1 inch.

21. The condom of claim 18 wherein said closure portion has a length not less than ¾ inch.

22. The condom of claim 18 wherein said closure portion has a length of not less than 1/32 inch.

23. The condom of claim 18 wherein the circumference of said sack portion is equal to or greater than 110% and not more than 175% of the circumference of said closure portion.

24. The condom of claim 23 wherein said condom is made of a material selected from the group consisting of natural rubber latex and thermoplastic elastomers.

25. The condom of claim 24 wherein said material is polyurethane.

26. The condom of claim 18 wherein the circumference of said sack portion is greater than 125% and less than 150% of the circumference of the said closure portion.

27. The condom of claim 26 wherein said condom is made of a material selected from the group consisting of natural rubber latex and thermoplastic elastomers.

28. The condom of claim 27 wherein said material is polyurethane.

29. A condom having an outer and inner surface and having a generally tubular shaped portion attached to a loose fitting sack portion closed at one end comprising:

a closure portion being resiliently stretchable and dimensioned for secure attachment when used to assure sealing and prevention of slippage, a loose-fitting sack portion having a closed end and an open end and having a length between said closed end and said open end, said closure portion being tubular and having a first end joined to the open end of the loose-fitting sack portion and a second end remote from said first end, said closure portion having a substantially uniform circumference which is less than the circumference of said sack portion, said loose-fitting sack portion having a lubricant on the outer surface and being easy to apply and unrestrained when used, said closure portion and said sack portion having a length of greater than about 3 9/16 inches, and said closure portion having a length between said first end and said second end which is less that the length of said sack portion, whereby the shaft of the user below the glands is exposed and movement and stimulation within the loose fitting sack portion of the condom.

30. The condom of claim 29 wherein the circumference of said sack portion is equal to or greater than 110% and not more than 175% of the circumference of said closure portion.

31. The condom of claim 30 wherein the circumference of said sack portion is greater than 125% and less than 150% of the circumference of said closure portion.

32. The condom of claim 29 wherein said condom is made of a material selected from the group consisting of natural latex rubber and thermoplastic elastomers.

33. The condom of claim 29 wherein said condom is made of polyurethane.

34. The condom of claim 29 wherein said closure portion has a length of not less than 1 inch.

35. The condom of claim 29 wherein said closure portion has a length of not less than ¾ inch.

36. The condom of claim 29 wherein said closure portion has a length of not less than 1/32 inch.

* * * * *